US010905329B2

(12) United States Patent
Bar-Tal et al.

(10) Patent No.: US 10,905,329 B2
(45) Date of Patent: Feb. 2, 2021

(54) MULTI-FUNCTION CONDUCTING ELEMENTS FOR A CATHETER

(71) Applicant: BIOSENSE WEBSTER (ISRAEL) LTD., Yokneam (IL)

(72) Inventors: Meir Bar-Tal, Haifa (IL); Michael Levin, Haifa (IL); Avi Reuveni, Givat Shmuel (IL); Debby Esther Highsmith, Laguna Niguel, CA (US); Ariel Garcia, Glendora, CA (US); Daniel Osadchy, Haifa (IL); Shmuel Auerbach, Kerem Maharal (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 804 days.

(21) Appl. No.: 15/359,838

(22) Filed: Nov. 23, 2016

(65) Prior Publication Data
US 2017/0354364 A1 Dec. 14, 2017

Related U.S. Application Data

(63) Continuation-in-part of application No. 15/177,775, filed on Jun. 9, 2016.

(51) Int. Cl.
*A61B 18/18* (2006.01)
*A61B 18/00* (2006.01)
(Continued)

(52) U.S. Cl.
CPC .......... *A61B 5/0036* (2018.08); *A61B 5/0422* (2013.01); *A61B 5/062* (2013.01);
(Continued)

(58) Field of Classification Search
CPC ..... A61B 5/4836; A61B 34/20; A61B 5/0422; A61B 5/062; A61B 5/6853; A61B 5/6858;
(Continued)

(56) References Cited

U.S. PATENT DOCUMENTS 5,411,025 A 5/1995 Webster, Jr.
5,505,730 A 4/1996 Edwards
(Continued)

FOREIGN PATENT DOCUMENTS

EP 2 682 157 A1 1/2014
WO WO 2012/092016 A1 7/2012

OTHER PUBLICATIONS

European Search Report dated Oct. 20, 2017 in corresponding European Patent Application No. 17175072.2.
(Continued)

*Primary Examiner* — Joseph A Stoklosa
*Assistant Examiner* — Brian M Antiskay

(57) ABSTRACT

Described embodiments include an apparatus that includes an expandable structure, configured for insertion into a body of a subject, and a plurality of conducting elements coupled to the expandable structure. Each of the conducting elements comprises a respective coil and has an insulated portion that is electrically insulated from tissue of the subject, and an uninsulated portion configured to exchange signals with the tissue, while in contact with the tissue. Other embodiments are also described.

17 Claims, 3 Drawing Sheets

(51) Int. Cl.
  *A61B 5/00* (2006.01)
  *A61B 5/042* (2006.01)
  *A61B 5/06* (2006.01)
  *A61B 34/20* (2016.01)
  *A61B 18/14* (2006.01)

(52) U.S. Cl.
  CPC .......... *A61B 5/4836* (2013.01); *A61B 5/6853* (2013.01); *A61B 5/6858* (2013.01); *A61B 5/7445* (2013.01); *A61B 18/1492* (2013.01); *A61B 34/20* (2016.02); *A61B 5/4848* (2013.01); *A61B 2018/0022* (2013.01); *A61B 2018/00267* (2013.01); *A61B 2018/00351* (2013.01); *A61B 2018/00577* (2013.01); *A61B 2018/00821* (2013.01); *A61B 2018/00875* (2013.01); *A61B 2034/2053* (2016.02)

(58) Field of Classification Search
  CPC .............. A61B 5/7445; A61B 18/1492; A61B 2034/2053; A61B 5/4848; A61B 2018/0022; A61B 2018/00267; A61B 2018/00351; A61B 2018/00577; A61B 2018/00821; A61B 2018/00875
  USPC ........ 600/372–374, 377, 381, 407, 422–424, 600/434–435, 508–509; 606/13–14, 606/32–34
  See application file for complete search history.

(56) References Cited

U.S. PATENT DOCUMENTS

| | | | |
|---|---|---|---|
| 6,272,371 B1 | 8/2001 | Shlomo | |
| 6,511,478 B1 | 1/2003 | Burnside et al. | |
| 6,785,571 B2* | 8/2004 | Glossop | A61B 90/36 600/424 |
| 6,892,091 B1 | 5/2005 | Ben-Haim et al. | |
| 7,697,972 B2* | 4/2010 | Verard | A61B 1/00071 600/407 |
| 8,097,926 B2 | 1/2012 | De Graff et al. | |
| 8,918,184 B1 | 12/2014 | Torgerson et al. | |
| 9,060,756 B2 | 6/2015 | Bencini et al. | |
| 9,179,963 B2 | 11/2015 | Ben-Ezra et al. | |
| 2002/0111618 A1* | 8/2002 | Stewart | A61B 18/1492 606/41 |
| 2003/0093067 A1 | 5/2003 | Panescu | |
| 2006/0025677 A1 | 2/2006 | Verard et al. | |
| 2008/0039790 A1* | 2/2008 | Hasebe | A61B 18/04 604/113 |
| 2011/0118590 A1 | 5/2011 | Zhang | |
| 2011/0264000 A1 | 10/2011 | Paul et al. | |
| 2012/0017923 A1* | 1/2012 | Sobe | A61B 34/20 128/899 |
| 2012/0172761 A1* | 7/2012 | Meller | A61B 5/062 600/585 |
| 2012/0323235 A1* | 12/2012 | Danek | A61B 18/08 606/33 |
| 2013/0281997 A1* | 10/2013 | Davie | A61B 5/0422 606/21 |
| 2013/0296679 A1* | 11/2013 | Condie | A61B 5/6856 600/374 |
| 2014/0051968 A1* | 2/2014 | Isham | A61N 5/10 600/407 |
| 2014/0058371 A1* | 2/2014 | Krishnan | A61B 17/12013 606/27 |
| 2014/0309512 A1* | 10/2014 | Govari | A61B 18/1492 600/374 |
| 2015/0057519 A1 | 2/2015 | Ben-David et al. | |
| 2015/0119670 A1 | 4/2015 | Madjarov et al. | |
| 2015/0157391 A1 | 6/2015 | Ben-Ezra et al. | |
| 2015/0216591 A1* | 8/2015 | Cao | A61B 18/1492 606/41 |
| 2015/0238275 A1* | 8/2015 | Kung | A61B 5/1076 600/424 |
| 2015/0250424 A1* | 9/2015 | Govari | A61B 5/6858 600/373 |
| 2015/0327921 A1* | 11/2015 | Govari | A61B 5/0422 600/373 |
| 2015/0366608 A1 | 12/2015 | Weber et al. | |
| 2018/0000420 A1* | 1/2018 | Romanowski | A61B 5/036 |
| 2018/0296114 A1* | 10/2018 | Welsh | A61B 5/061 |
| 2018/0303414 A1* | 10/2018 | Toth | A61B 5/6858 |

OTHER PUBLICATIONS

European Search Report dated Oct. 24, 2017 in corresponding European Patent Application No. 17174936.9.

European Search Report dated Dec. 4, 2018, Application No. EP 18 19 2797.1.

European Search Report dated Jun. 16, 2020, Application No. EP 20 15 0359.6.

\* cited by examiner

MULTI-FUNCTION CONDUCTING ELEMENTS FOR A CATHETER

CROSS-REFERENCE TO RELATED APPLICATIONS

The present application is a continuation-in-part of, and claims the benefit of, U.S. patent application Ser. No. 15/177,775, entitled "Dual-function sensors for a basket catheter," filed Jun. 9, 2016, whose disclosure is incorporated herein by reference.

FIELD OF THE INVENTION

Embodiments of the present invention relate generally to the field of medical devices, and particularly to catheters for recording intracardiac electrocardiogram (ECG) signals and/or ablating cardiac tissue.

BACKGROUND

In some applications, a basket catheter, comprising a large number of electrodes disposed on a plurality of splines, is used to acquire intracardiac electrocardiogram (ECG) signals. Such signals may be used, for example, to construct an electroanatomical map of the heart.

In other applications, a balloon catheter, comprising a plurality of electrodes disposed on a balloon, is used to ablate cardiac tissue, and/or to acquire intracardiac ECG signals.

US Patent Application Publication 2011/0118590, whose disclosure is incorporated herein by reference, describes an interventional system for internal anatomical examination that includes a catheterization device for internal anatomical insertion. The catheterization device includes at least one magnetic field sensor for generating an electrical signal in response to rotational movement of the at least one sensor about an axis through the catheterization device within a magnetic field applied externally to patient anatomy, and a signal interface for buffering the electrical signal for further processing. A signal processor processes the buffered electrical signal to derive a signal indicative of angle of rotation of the catheterization device relative to a reference. The angle of rotation is about an axis through the catheterization device. A reproduction device presents a user with data indicating the angle of rotation of the catheterization device.

US Patent Application Publication 2003/0093067, whose disclosure is incorporated herein by reference, describes systems and methods for imaging a body cavity and for guiding a treatment element within a body cavity. A system may include an imaging subsystem having an imaging device and an image processor that gather image data for the body cavity. A mapping subsystem may be provided, including a mapping device and a map processor, to identify target sites within the body cavity, and provide location data for the sites. The system may also include a location processor coupled to a location element on a treatment device to track the location of the location element. The location of a treatment element is determined by reference to the location element. A treatment subsystem including a treatment device having a treatment element and a treatment delivery source may also be provided. A registration subsystem receives and registers data from the other subsystems, and displays the data.

U.S. Pat. No. 6,272,371, whose disclosure is incorporated herein by reference, describes an invasive probe apparatus including a flexible elongate probe having a distal portion adjacent to a distal end thereof for insertion into the body of a subject, which portion assumes a predetermined curve form when a force is applied thereto. First and second sensors are fixed to the distal portion of the probe in known positions relative to the distal end, which sensors generate signals responsive to bending of the probe. Signal processing circuitry receives the bend responsive signals and processes them to find position and orientation coordinates of at least the first sensor, and to determine the locations of a plurality of points along the length of the distal portion of the probe.

US Patent Application Publication 2006/0025677, whose disclosure is incorporated herein by reference, describes a surgical navigation system for navigating a region of a patient that may include a non-invasive dynamic reference frame and/or fiducial marker, sensor tipped instruments, and isolator circuits. The dynamic reference frame may be placed on the patient in a precise location for guiding the instruments. The dynamic reference frames may be fixedly placed on the patient. Also the dynamic reference frames may be placed to allow generally natural movements of soft tissue relative to the dynamic reference frames. Also methods are provided to determine positions of the dynamic reference frames. Anatomical landmarks may be determined intra-operatively and without access to the anatomical structure.

U.S. Pat. No. 6,892,091, whose disclosure is incorporated herein by reference, describes an apparatus and method for rapidly generating an electrical map of a chamber of a heart that utilizes a catheter including a body having a proximal end and a distal end. The distal end has a distal tip and an array of non-contact electrodes having a proximal end and a distal end and at least one location sensor. Preferably, two location sensors are utilized. The first location sensor is preferably proximate to the catheter distal tip and the second location sensor is preferably proximate to the proximal end of the non-contact electrode array. The catheter distal end further preferably includes a contact electrode at its distal tip. Preferably, at least one and preferably both of the location sensors provide six degrees of location information. The location sensor is preferably an electromagnetic location sensor. The catheter is used for rapidly generating an electrical map of the heart within at least one cardiac cycle and preferably includes cardiac ablation and post-ablation validation.

SUMMARY OF THE INVENTION

There is provided, in accordance with some embodiments of the present invention, apparatus that includes an expandable structure, configured for insertion into a body of a subject, and a plurality of conducting elements coupled to the expandable structure. Each of the conducting elements includes a respective coil, and has an insulated portion that is electrically insulated from tissue of the subject, and an uninsulated portion configured to exchange signals with the tissue, while in contact with the tissue.

In some embodiments, the expandable structure includes a balloon.

In some embodiments, the expandable structure includes a basket.

In some embodiments, each of the conducting elements includes an electrode connected to the coil, the electrode being configured to exchange the signals with the tissue, and the coil being configured to carry the exchanged signals.

In some embodiments, the coil is situated proximally to the electrode to which the coil is connected.

In some embodiments, the coil is a single-loop coil.

In some embodiments, the coil is a helical coil.

In some embodiments, the coil is flat.

In some embodiments, the apparatus further includes two leads connected to each conducting element of the conducting elements, configured to carry the signals between the conducting element and a proximal end of the apparatus.

In some embodiments, at least part of each conducting element of the conducting elements has an electrical resistance that varies in response to strain to which the conducting element is subjected inside the body of the subject.

In some embodiments, each of the conducting elements includes a thermocouple junction.

In some embodiments, the coil includes the uninsulated portion.

There is further provided, in accordance with some embodiments of the present invention, a method that includes receiving from a conducting element, via two leads that connect the conducting element to a proximal end of a catheter, a voltage difference that was induced across the conducting element by a magnetic field. The method further includes, in response to the voltage difference, ascertaining a location of the conducting element, and, while the conducting element is in contact with tissue of a subject, exchanging a signal with the tissue via the conducting element and at least one of the leads.

In some embodiments, the signal is an electrocardiogram (ECG) signal, and exchanging the signal includes acquiring the ECG signal from the tissue.

In some embodiments, the signal is an ablation signal, and exchanging the signal includes passing the ablation signal into the tissue.

In some embodiments, exchanging the signal includes exchanging the signal while the conducting element is inside a body of a subject.

In some embodiments, the conducting element is a single-loop coil.

In some embodiments, the conducting element is a helical coil.

In some embodiments, the voltage difference is a first voltage difference, and the method further includes measuring a temperature, by measuring a second voltage difference across the leads.

In some embodiments, the method further includes measuring a strain exerted on the conducting element, by measuring an electrical resistance of the conducting element.

In some embodiments, the method further includes measuring an impedance between the conducting element and a patch coupled to skin of the subject, by passing an electric current between the conducting element and the patch, wherein the ascertaining of the location is further in response to the measured impedance.

The present invention will be more fully understood from the following detailed description of embodiments thereof, taken together with the drawings, in which:

DETAILED DESCRIPTION OF EMBODIMENTS

Overview

Figure 1:
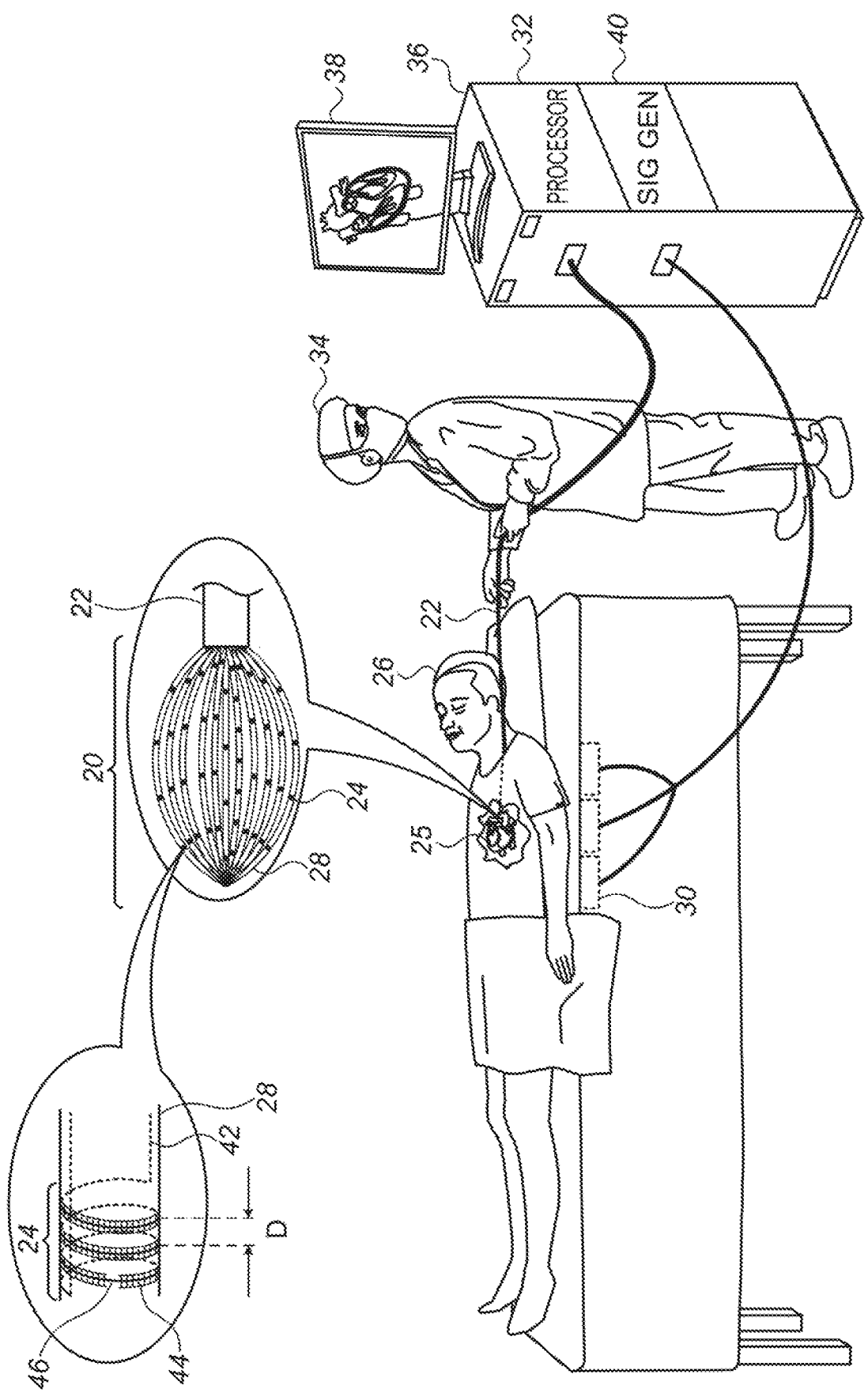
FIG. 1 is a schematic illustration of a basket catheter, in accordance with some embodiments of the present invention.

Embodiments described herein include catheters comprising conducting elements that perform, e.g., simultaneously, a plurality of functions. For example, the conducting elements may function as electromagnetic sensors, by outputting, in the presence of a magnetic field, signals that may be used to ascertain the location and/or orientation of the catheter on which the conducting elements are disposed. In addition, the conducting elements may function as electrodes. For example, the conducting elements may be used to exchange signals with tissue, such as by acquiring ECG signals from tissue, or passing ablating signals into tissue. Alternatively or additionally, the conducting elements may be used to measure impedance, temperature, strain, and/or other relevant parameters.

More particularly, embodiments described herein include a basket catheter that may be used, for example, to build an electroanatomical map. The basket catheter comprises a plurality of splines at its distal end, and further comprises a plurality of helical conducting elements, which are disposed on the splines. During the electroanatomical mapping procedure, the helical conducting elements function as inductors, in that a generated magnetic field induces respective voltage differences across the conducting elements. Based on the induced voltage differences, the respective locations and orientations of the conducting elements—and hence, the location and orientation of the basket catheter—may be precisely determined.

The helical conducting elements additionally function as electrodes for acquiring ECG signals, such that it may not be necessary to equip the basket catheter with separate ECG-acquiring electrodes. For example, an electrically-insulative layer may cover the majority of each of the helical conducting elements, but leave a small portion of each of the helical conducting elements exposed. This exposed portion, when brought into contact with the intracardiac tissue, acquires ECG signals from the tissue.

The helical conducting elements described herein may thus function in two capacities—e.g., simultaneously—during a single procedure. First, they may function as ECG electrodes, by sensing the intracardiac ECG signals. Second, they may function as magnetic-field sensors, by outputting location-indicating signals (in the form of the above-described induced voltages) in response to the generated magnetic field. The conducting elements may thus be described as ECG electrodes that additionally function as magnetic-field sensors, or as magnetic-field sensors that additionally function as ECG electrodes. (Notwithstanding the above, in some embodiments, the conducting elements are used only as magnetic-field sensors, and separate electrodes coupled to the splines are used to acquire the ECG signals.)

Other embodiments described herein include a balloon catheter, comprising a balloon, and a plurality of conducting elements coupled to the balloon. Each one of the conducting elements comprises an electrode, configured to exchange signals with tissue, and a coil that is connected to the electrode. The coil carries the signals that are exchanged with the tissue, and also outputs signals (in the form of induced voltages) in response to a magnetic field. The conducting elements thus function as both magnetic-field sensors and as electrodes. Alternatively or additionally, the conducting elements may measure other parameters, such as impedance, temperature, or strain.

Embodiments described herein further include circuitry for processing signals received from the multi-function conducting elements. For example, the circuitry described herein may generate, based on signals received from the above-described helical conducting elements, a plurality of outputs, which are used by a processor to construct an electroanatomical map. These outputs include a plurality of first outputs, which indicate the electrical activity of the tissue, a plurality of second outputs, which indicate the respective induced voltage differences across the conducting elements, and a plurality of third outputs, which indicate the proximity to the tissue of each of the conducting elements.

Apparatus Description

Reference is initially made to FIG. 1, which is a schematic illustration of a basket catheter 22, in accordance with some embodiments of the present invention. FIG. 1 depicts a physician 34 using basket catheter 22 to perform an electroanatomical mapping of a heart 25 of a subject 26. During the mapping procedure, the distal end of the catheter, which comprises a basket 20 of splines 28, is inserted into heart 25. The splines are then brought into contact with the intracardiac tissue, and conducting elements 24 on the splines acquire intracardiac ECG signals. A console 36, which is connected to the basket catheter and comprises a computer processor 32, receives these ECG signals.

While the intracardiac ECG signals are being acquired, a magnetic field is generated by a plurality of magnetic-field generators 30 located underneath subject 26 or otherwise in the vicinity of the subject. (As shown in FIG. 1, a signal generator ("SIG GEN") 40 in console 36 may cause generators 30 to generate the magnetic field by supplying an alternating current to the generators.) The magnetic field induces voltage differences across conducting elements 24. The induced voltage differences are received by the console, and, based on the induced voltages, processor 32 ascertains the position of each of the conducting elements. Processor 32 then constructs an electroanatomical map of the heart, based on the ECG signals (which indicate the electrical activity of the intracardiac tissue) and the voltages received from the helical conducting elements (which indicate the respective locations of the sources of the ECG signals). Such a map may be displayed on a monitor 38 for viewing by physician 34, and/or stored for later analysis.

Splines 28 may be arranged to define any suitably-shaped basket, such as the spheroidal basket shown in FIG. 1. FIG. 1 shows an embodiment in which a plurality of helical conducting elements 24 are disposed on the surface of each of the splines. The top-left portion of the figure shows an enlarged view of a single such helical conducting element. In this enlarged view, the solid portion of the conducting element corresponds to the portion of the conducting element that is on the near side of the spline, facing the viewer. The dotted portion corresponds to the portion of the conducting element that is on the far side of the spline, facing away from the viewer. Each of the two terminals of each of the conducting elements is typically connected to the console via a wire 42 which passes through the interior of the spline.

In some embodiments, the conducting elements are printed onto the splines. For example, each of the conducting elements may comprise electrically-conductive paint that is helically painted onto the splines. In other embodiments, the conducting elements comprise wires that are wound (i.e., coiled) around, and glued or otherwise attached to, the splines. In any case, for embodiments in which the helical conducting elements are on the surface of the splines, an electrically-insulative layer 44 typically covers at least a majority of each of the helical conducting elements. Electrically-insulative layer 44 prevents the turns of any given conducting element from being shorted with each other.

Typically, the electrically-insulative layer does not cover a portion of exactly one respective turn of each of the helical conducting elements. Thus, the electrically-insulative layer prevents shorting of the turns (in that no more than one turn of each conducting element is exposed), but also allows the conducting elements to acquire ECG signals. For example, the enlarged portion of FIG. 1 shows an embodiment in which the electrically-insulative layer exposes a portion 46 of the conducting element. Exposed portion 46 may be brought into contact with tissue, in order to acquire an ECG signal.

As noted above, the exposed portion of the conducting element is confined to one turn of the conducting element. This means that the distance between the distalmost exposed portion of the conducting element and the proximalmost exposed portion of the conducting element is less than the distance D that separates between successive turns of the conducting element.

In some embodiments, the electrically-insulative layer is contiguous across a plurality of conducting elements. In other embodiments, as depicted in FIG. 1, the electrically-insulative layer is discontiguous, such that no portion of the electrically-insulative layer covers more than one of the conducting elements. Similarly, for any given conducting element, the cover provided by the electrically-insulative layer may be contiguous or discontiguous. As an example of the latter, in FIG. 1, the conducting element is covered by two separate, disjoint portions of the electrically-insulative layer, these portion being on respective opposite sides of exposed portion 46 of the conducting element.

In some embodiments, alternatively to being disposed on the splines as in FIG. 1, the conducting elements are contained within the splines. In such embodiments, the splines, being made of an electrically-insulative material (such as plastic), provide the "cover" that prevents the conducting elements from being shorted. For embodiments in which the conducting elements are additionally used to acquire ECG signals, the splines are shaped to define a plurality of openings that expose a portion of exactly one respective turn of each of the helical conducting elements. In other words, such embodiments are analogous to the embodiments described above, with the surface of the spline functioning analogously to electrically-insulative layer 44 in preventing shorting of the conducting elements, but also, optionally, providing for ECG-signal acquisition.

Figure 2:
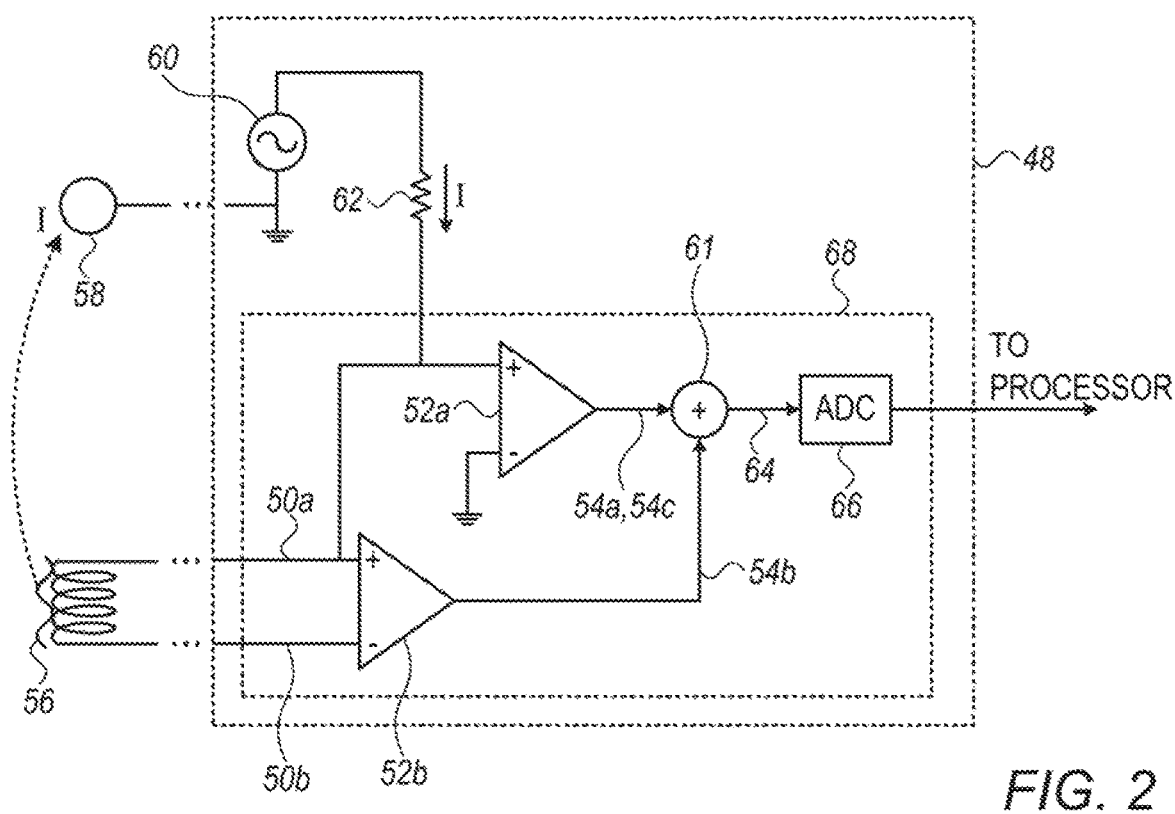
FIGS. 2-3 are schematic illustrations of circuitry for processing signals received from conducting elements, in accordance with some embodiments of the present invention.

Reference is now made to FIG. 2, which is a schematic illustration of circuitry 48 for processing signals received from conducting elements 24, in accordance with some embodiments of the present invention. Circuitry 48 is typically located within console 36, between the catheter-console interface and the processor. As shown in FIG. 2, circuitry 48 is connected to each helical conducting element 24, typically via exactly two connections (or "leads") connected to the conducting element: a first connection 50a to one terminal of the conducting element, and a second connection 50b to the other terminal of the conducting element. As further described below, circuitry 48 generates outputs based on signals received, via connections 50a and

50b, from each helical conducting element. Based on these outputs, processor 32 constructs an electroanatomical map of the subject's heart.

Typically, circuitry 48 comprises a first differential amplifier 52a and a second differential amplifier 52b. Connections 50a and 50b are connected to second differential amplifier 52b, while one of the connections—e.g., first connection 50a—is also connected to first differential amplifier 52a. Connections 50a and 50b thus carry inputs to the differential amplifiers, as further described below.

As described above, the exposed portion of each conducting element 24 is brought into contact with intracardiac tissue 56, such that an ECG voltage (referred to above as an "ECG signal") is transferred to the conducting element from the tissue. (The ECG voltage is generally constant across the conducting element, i.e., the ECG voltage at the terminal of the conducting element is not significantly different from the ECG voltage at the exposed portion of the conducting element.) First connection 50a carries the ECG voltage to first differential amplifier 52a, which generates a first output 54a based on the ECG voltage, by amplifying a difference between the received ECG voltage and a reference voltage. The processor derives electrical-activity information from first output 54a, and uses this information to build the electroanatomical map. Typically, the reference voltage is the voltage at a reference electrode 58 disposed on the basket catheter, e.g., on a central spline of the catheter shaft (not shown in FIG. 1). (In FIG. 2, reference electrode 58 is connected to ground, such that the reference voltage is ground.)

Connection 50a also carries, to second differential amplifier 52b, the voltage induced by the magnetic field at one terminal of the conducting element, while connection 50b carries the voltage induced at the other terminal. In other words, connections 50a and 50b collectively carry, to the second differential amplifier, the voltage difference that is induced across the conducting element. Based on this voltage difference, second differential amplifier 52b generates a second output 54b, by amplifying the voltage difference. Second output 54b includes anatomical information, in that the second output indicates the position of the conducting element, and hence, the location of the source of the ECG signal. The processor derives this anatomical information from the second output, and then, in building the electroanatomical map, combines this anatomical information with the electrical-activity information derived from the first output.

Typically, circuitry 48 further comprises a current source, or, as in FIG. 2, a voltage source 60 in series with a resistor 62, which together function as a current source. The current source passes a current "I" over connection 50a and between the conducting element and reference electrode 58 (or a different reference electrode that is not used for the ECG reference voltage). During the passing of the current, the voltage on the conducting element indicates the impedance that is seen by the conducting element; the higher the voltage, the higher the impedance. The impedance, in turn, indicates the proximity of the conducting element to the tissue; the higher the impedance, the greater the proximity. Thus, the voltage on the conducting element indicates the proximity of the conducting element to the tissue. The first differential amplifier generates a third output 54c based on this proximity-indicating voltage, by amplifying the difference between the proximity-indicating voltage and the reference voltage. The processor then uses the third output to build the electroanatomical map. In particular, the processor first derives, from the third output, the proximity of the conducting element to the tissue. The processor then decides whether to accept the first (electrical-activity-related) output, based on the proximity. For example, the processor may compare the proximity to a threshold, and accept the first output only if the proximity is greater than the threshold (i.e., the distance between the conducting element and the tissue is sufficiently small).

It is noted that the ECG voltage, the induced voltage, and the proximity-indicating voltage are of sufficiently different frequencies, such that the three voltages may be simultaneously carried on connection 50a (and hence, simultaneously received by the circuitry). Thus, first output 54a, second output 54b, and third output 54c may be generated at the same time. In some embodiments, an adder 61 adds the first output, the second output, and the third output, yielding a combined output 64 having a plurality of components at various frequencies. Combined output 64 is then passed to an analog-to-digital converter (ADC) 66, which converts the combined output to a digital signal that is passed to the processor.

Although, for simplicity, only a single helical conducting element 24 is shown in FIG. 2, basket catheter 22 typically comprises a large number of helical conducting elements. On this note, reference is now made to FIG. 3, which is a schematic illustration of circuitry 48, in accordance with some embodiments of the present invention.

Figure 3:
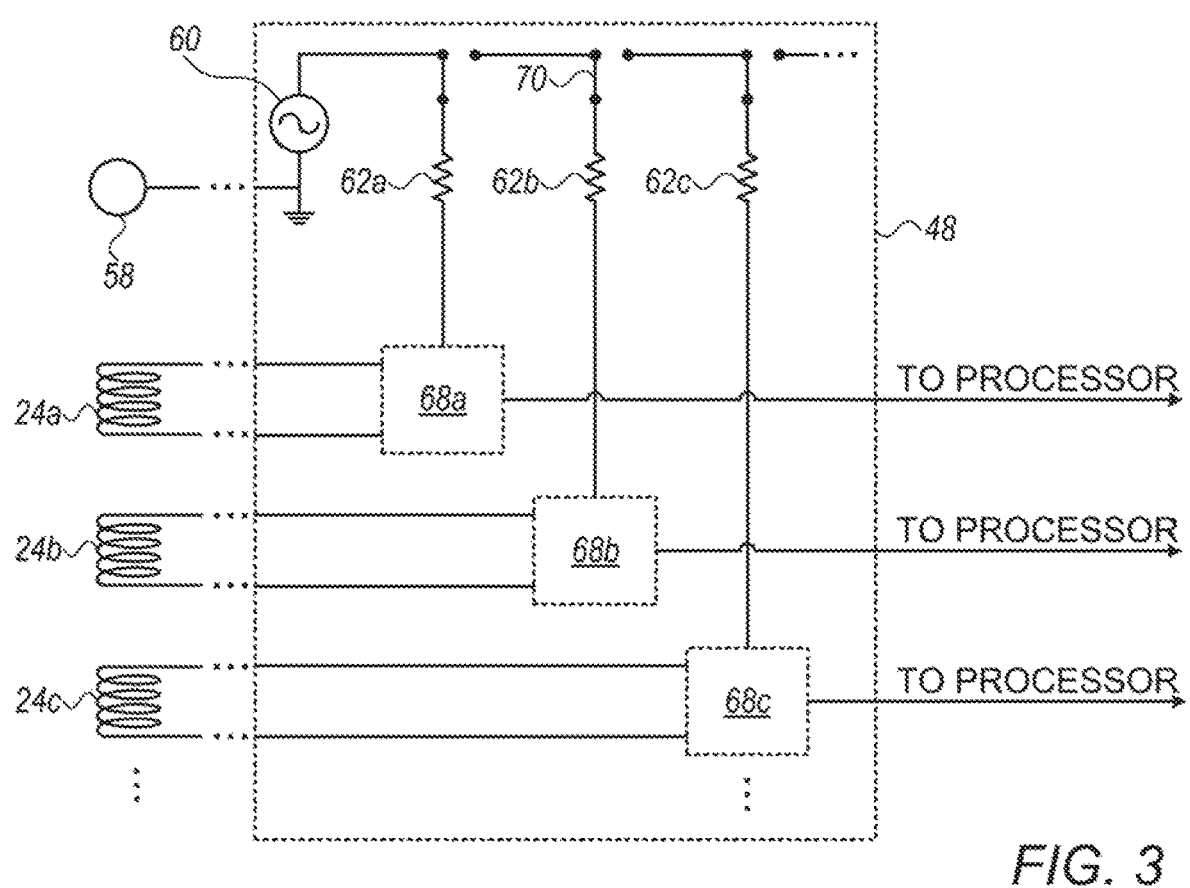

FIG. 3 shows a way in which the configuration of circuitry 48 shown in FIG. 2 may be extended to handle a large number of inputs from a large number of helical conducting elements. In particular, in FIG. 3, a block 68 of circuitry that is shown in FIG. 2 is replicated for each of the conducting elements. Thus, in FIG. 3, a conducting element 24a connects to a block 68a of circuitry, a conducting element 24b connects to a block 68b, and a conducting element 24c connects to a block 68c. Similarly, resistor 62 is replicated for each of the conducting elements, such that voltage source 60 may be connected to block 68a via a resistor 62a, to block 68b via a resistor 62b, or to block 68c via a resistor 62c. (Typically, switches 70 ensure that the voltage source is connected to no more than one block at a time.) Thus, for example, to pass a current between conducting element 24a and the reference electrode, the voltage source is connected to block 68a.

As indicated by the three-dot sequences in the figure, the configuration shown in FIG. 3 may be extended to handle any number of conducting elements.

It is emphasized that the principles described herein may be applied in many ways. For example, the scope of the present disclosure includes using each of one or more coils, and/or other conducting elements, for both (i) magnetic tracking, and (ii) exchanging signals with tissue, in any relevant application. (Circuitry described with reference to FIGS. 2-3 may be modified as appropriate to suit the application.) Exchanging signals with tissue includes, for example, acquiring ECG signals as described above, and/or passing ablating signals into tissue. (In the latter case, the same leads that carry the induced voltage from the conducting element may be used to deliver the ablating signal to the conducting element.) Moreover, the multi-function sensors described herein may be disposed on any suitable apparatus, including, for example, an intrabody device such as a lasso catheter, balloon catheter, or other type of catheter.

Figure 4:
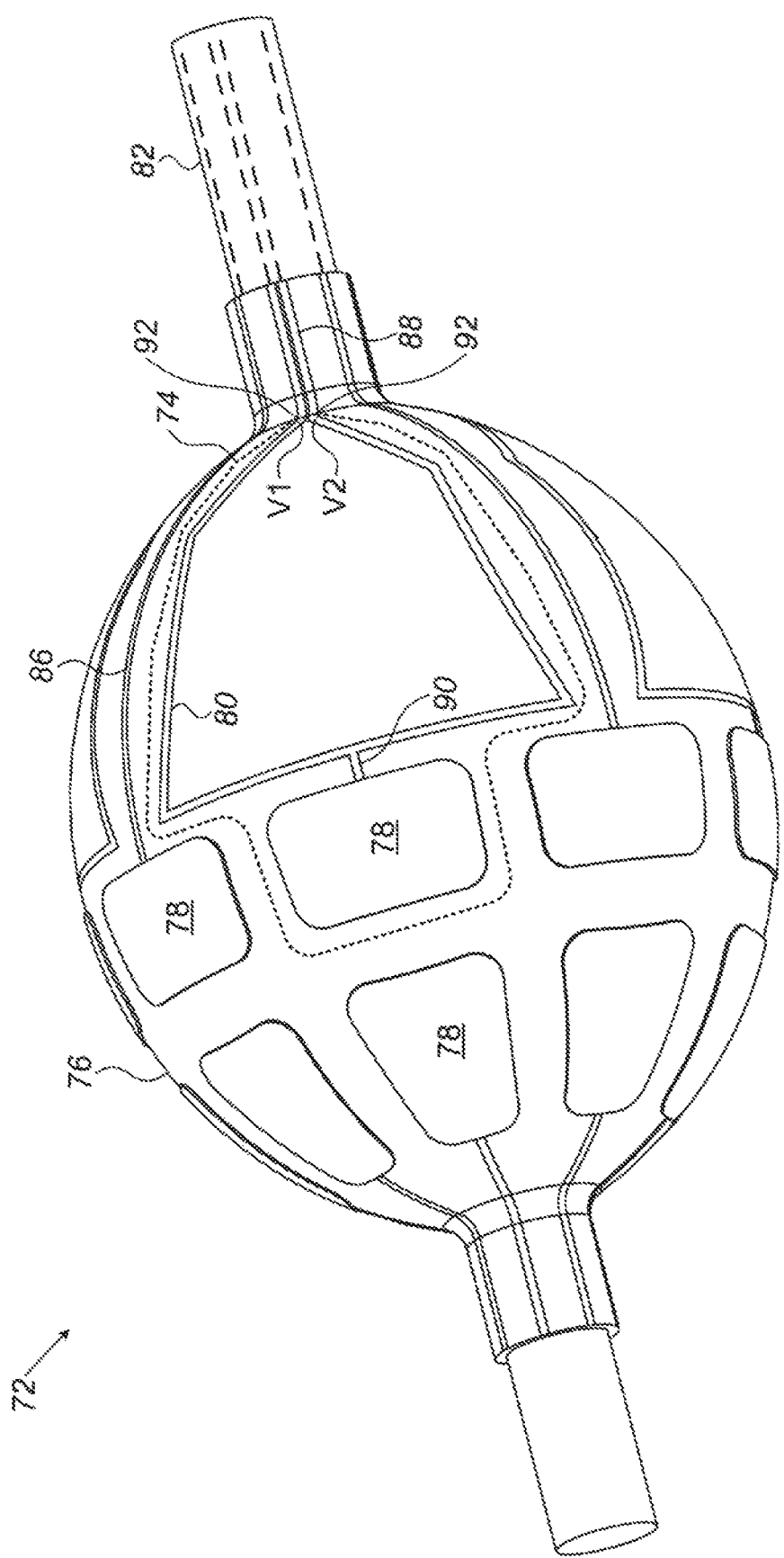
FIG. 4 is a schematic illustration of a catheter comprising multi-function conducting elements, in accordance with some embodiments of the present invention.

For example, reference is now made to FIG. 4, which is a schematic illustration of a catheter 72 comprising multi-function conducting elements 74, in accordance with some embodiments of the present invention. Catheter 72, which may be described as a "balloon catheter," comprises a balloon 76, located at or near the distal end of the shaft 82 of the catheter, and a plurality of multi-function conducting elements coupled to balloon 76. Conducting elements 74 may, for example, be printed onto the surface of the balloon, or may be coupled to the balloon in any other suitable way.

In some embodiments, each conducting element 74 comprises an electrode 78, configured to exchange signals with tissue, and a coil 80 electrically connected to electrode 78. As opposed to coils 80, which are generally electrically insulated from the tissue, electrodes 78 are not insulated, such that the electrodes may make electrical contact with the tissue. Leads (or "connections") 88, which run proximally-distally through shaft 82, connect the conducting elements to the proximal end of the catheter, which is connected to console 36 (FIG. 1). As shown in FIG. 4, catheter 72 may also comprise one or more additional electrodes 78, which are not coupled to coils, but instead, are coupled directly to leads 86.

Following the insertion of catheter 72 into the heart of a subject (as generally depicted in FIG. 1 for basket catheter 22), balloon 76 is inflated and one or more electrodes 78 are brought into contact with the intracardiac tissue. The electrodes then exchange signals with the tissue, e.g., by acquiring intracardiac ECG signals, and/or passing ablating signals into the tissue. Each such signal is carried to or from the relevant electrode by the coil and/or lead to which the electrode is attached. For example, in the case of an electrode belonging to a multi-function conducting element, each exchanged signal is carried between the conducting element and the proximal end of the catheter by a lead 88, and between the lead and the electrode by coil 80. (Coil 80 thus functions as a conductive trace.)

As shown in FIG. 4, leads 88 may be integrally formed with, and hence entirely continuous with, the coils, such that each coil may be described as the distal looped end of a single lead that runs distally through shaft 82, forms a loop along the surface of the balloon, and then returns, passing proximally, through the catheter shaft.

Coils 80 also output location-indicating signals in response to a magnetic field. In particular, in the presence of an externally-applied magnetic field, an alternating current (AC) voltage is induced in the coil, creating an AC voltage difference between the two terminals 92 of each coil, this voltage difference indicating the location and/or orientation of the coil relative to magnetic-field generators 30 (FIG. 1). For example, FIG. 4 shows an induced voltage difference V2−V1 between terminals 92 of one of the coils. This voltage difference is carried by leads 88 to the console. Processor 32 receives the voltage difference, and, in response to the voltage difference, ascertains the location and/or orientation of the coil (and hence, of the electrode to which the coil is connected).

(The "terminals" of the coil are the two points, at the proximal end of the coil, at which the coil becomes effectively closed, such that the coil meets, or "becomes," leads 88. At the proximal end of the coil, leads 88 may be in mechanical (but not electrical) contact with one another, and, in some embodiments, may cross over one another.)

The location-indicating signals from the conducting elements may be used to guide the conducting elements to the appropriate location(s) for signal exchange. For example, while a particular conducting element is in contact with tissue, a location-indicating signal may be received from the conducting element. If the location indicated by the location-indicating signal is a desired location for signal exchange, a signal may be exchanged with the tissue via the conducting element (and in particular, the electrode belonging to the conducting element) and at least one of its leads. Otherwise, the position and/or orientation of catheter 72 may be adjusted as appropriate, prior to the signal exchange.

Each coil may be situated proximally or distally to the electrode to which the coil is connected. Typically, as shown, the coil is flat, i.e., it is not a barrel coil, such that the coil does not overly protrude from the surface of the balloon. Typically, as shown, each coil is a single-loop coil. In some embodiments, as shown, the coil is shaped to define a polygon, e.g., a five-sided polygon. Alternatively, the coil may have any other suitable shape, such as that of a circle or ellipse. As shown, the coil may be connected to the electrode (e.g., at the "base" of the polygon) by a connecting wire 90.

In some embodiments, each coil 80 also functions as an electrode. For example, each coil may comprise, in addition to an insulated portion that is electrically insulated from the tissue, an uninsulated portion. This uninsulated portion, while in contact with the tissue, exchanges signals, such as ECG signals and ablation signals, with the tissue. The coil thus performs at least three functions: (i) the exchange of signals with the tissue, (ii) the carrying of these signals to or from the tissue, and (iii) the output of voltage differences in response to a magnetic field. It is noted that a conducting element 74 that comprises such a coil does not necessarily comprise an electrode 78 that is separate from the coil, since the coil may already perform the function of electrode 78.

In some embodiments, at least part of each of the conducting elements has an electrical resistance that varies in response to strain to which the conducting element is subjected inside the body of the subject. For example, coil 80, in whole or in part, may be made of a biocompatible strain-sensitive material, and/or may have a form that renders the coil sensitive to strain. In such embodiments, the strain exerted on each of the conducting elements may be measured, by measuring the electrical resistance of the conducting elements. For example, a current of known amplitude (and a frequency different from that of the generated magnetic field) may be passed through each of the conducting elements via the leads connected thereto, and the resulting voltage between the proximal terminals of the leads may be measured. This voltage, divided by the amplitude of the current (and taking into account the electrical resistance of the leads), gives the electrical resistance of the conducting element, which in turn indicates the magnitude of the strain applied to the conducting element. The strain applied to the catheter may then be derived from the strains that were measured for the conducting elements.

Alternatively or additionally, each of the conducting elements may comprise a thermocouple junction. In other words, each of the conducting elements may comprise two portions, made of different metals, connected to one another at a temperature-sensing junction, such that each of the conducting elements functions as a thermocouple temperature sensor. For example, a portion of coil 80 may be made of copper, and another portion of the coil may be made of constantan, the copper and constantan being connected to one another at a thermocouple junction. Such a junction may be located, for example, at the distal end of coil 80, e.g., at the point at which coil 80 meets connecting wire 90. Alternatively, such a junction may be located anywhere else along coil 80, or along one of leads 88. In such embodiments, a thermocouple junction may be used to measure the temperature of the tissue and/or of the ambient environment. For example, while a thermocouple junction is contacting the subject's tissue, the temperature of the tissue may be measured, by measuring the voltage difference across the leads. (This voltage is a direct current (DC) voltage, such that it may be differentiated from the alternating voltage induced by the generated magnetic field.)

Alternatively or additionally, an electric current may be passed between the conducting element and a patch coupled to skin of the subject, such as to measure the impedance between the conducting element and the patch. Such an impedance measurement may be used, for example, for an impedance-based tracking system, whereby the location of the conducting element is ascertained in response to the measured impedance, alternatively or additionally to being ascertained in response to the voltage induced in the conducting element by a generated magnetic field.

It is noted that the above-described strain, temperature, and impedance measurements may also be performed by conducting elements 24, described above with respect to FIG. 1, as well as by any other suitable multi-function conducting elements. The multi-function conducting elements described herein may be coupled to an expandable structure, such as basket 20 of FIG. 1 or balloon 76 of FIG. 4, or to any other suitable tool.

It will be appreciated by persons skilled in the art that the present invention is not limited to what has been particularly shown and described hereinabove. Rather, the scope of embodiments of the present invention includes both combinations and subcombinations of the various features described hereinabove, as well as variations and modifications thereof that are not in the prior art, which would occur to persons skilled in the art upon reading the foregoing description. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. An apparatus, comprising:
   (a) an expandable structure, configured for insertion into a body of a subject; and
   (b) a plurality of conducting elements disposed on a surface of the expandable structure, each of the plurality of conducting elements comprising a respective coil having two terminals, each of the coils are configured to induce an alternating current (AC) voltage difference between the two terminals in response to an external magnetic field, each of the coils having:
      i) an insulated portion that is electrically insulated from tissue of the subject, and
      ii) an uninsulated portion connected electrically to the two terminals, the uninsulated portion comprises an electrode configured to exchange signals with the tissue of the subject while in contact with the tissue of the subject; and
   (c) a processor, the processor configured to:
      receive the exchanged signals from the electrode; and
      receive an output of the AC voltage difference between the two terminals in response to the external magnetic field.

2. The apparatus according to claim 1, wherein the expandable structure comprises a balloon.

3. The apparatus according to claim 1, wherein the expandable structure comprises a basket.

4. The apparatus according to claim 1, wherein each of the coils comprises a single-loop coil.

5. The apparatus according to claim 1, wherein each of the coils comprises a helical coil.

6. The apparatus according to claim 1, wherein each of the coils comprises a flat coil.

7. The apparatus according to claim 1, further comprising two leads connected to each of the plurality of conducting elements, configured to carry the signals between the corresponding conducting element and the processor.

8. The apparatus according to claim 1, wherein at least part of each conducting element of the plurality of conducting elements has an electrical resistance that varies in response to strain to which the corresponding conducting element is subjected inside the body of the subject.

9. The apparatus according to claim 1, wherein each of the plurality of conducting elements comprises a thermocouple junction.

10. A method, comprising:
    inserting an apparatus into a body of a subject, wherein the apparatus comprises: an expandable structure; a plurality of conducting elements disposed on a surface of the expandable structure, each of the plurality of conducting elements comprises a respective coil having two leads, each of the coils having an insulated portion that is electrically insulated from tissue of the subject, and an uninsulated portion connected electrically to the two leads, the uninsulated portion comprises an electrode; and a processor;
    positioning the plurality of conducting elements against the tissue of the subject;
    inducing an alternating current (AC) voltage difference across each of the coils in response to an external magnetic field;
    transmitting the AC voltage difference across each of the coils to the processor via respective two leads;
    ascertaining locations of the plurality of conducting elements in response to the AC voltage differences across the coils; and
    exchanging a signal with the tissue of the subject via the electrode and at least one of the two leads while the electrode is in contact with the tissue of the subject.

11. The method according to claim 10, wherein the signal comprises an electrocardiogram (ECG) signal, and wherein exchanging the signal comprises acquiring the ECG signal from the tissue of the subject via the processor.

12. The method according to claim 10, wherein the signal comprises an ablation signal, and wherein exchanging the signal comprises passing the ablation signal into the tissue of the subject.

13. The method according to claim 10, wherein the conducting element comprises a single-loop coil.

14. The method according to claim 10, wherein the conducting element comprises a helical coil.

15. The method according to claim 10, wherein the AC voltage difference is a first voltage difference, and wherein the method further comprises measuring a temperature, by measuring a second voltage difference across the two leads.

16. The method according to claim 10, further comprising measuring a strain exerted on at least one of the plurality of the conducting elements, by measuring an electrical resistance of the at least one of the plurality of conducting elements.

17. The method according to claim 10, further comprising measuring an impedance between the plurality of conducting elements and a patch coupled to skin of the subject, by passing an electric current between the plurality of conducting elements and the patch, wherein the ascertaining of the location is further in response to the measured impedance.

* * * * *